US009085416B2

(12) United States Patent
Beselt

(10) Patent No.: US 9,085,416 B2
(45) Date of Patent: Jul. 21, 2015

(54) PNEUMATICALLY-EXPANDABLE CABLE TRACK FOR SCANNING HEAD OF PAPER MACHINE OR OTHER SYSTEM

(71) Applicant: Honeywell International Inc., Morristown, NJ (US)

(72) Inventor: Ronald E. Beselt, Burnaby (CA)

(73) Assignee: Honeywell ASCA Inc., Mississauga, Ontario (CA)

( * ) Notice: Subject to any disclaimer, the term of this patent is extended or adjusted under 35 U.S.C. 154(b) by 124 days.

(21) Appl. No.: 13/874,430

(22) Filed: Apr. 30, 2013

(65) Prior Publication Data

US 2014/0318928 A1 Oct. 30, 2014

(51) Int. Cl.
*H01B 17/34* (2006.01)
*H01B 7/08* (2006.01)
*B65G 23/44* (2006.01)
*H01B 17/36* (2006.01)

(52) U.S. Cl.
CPC *B65G 23/44* (2013.01); *H01B 7/08* (2013.01); *H01B 17/34* (2013.01); *H01B 17/36* (2013.01)

(58) Field of Classification Search
CPC .......... H02G 15/24; H01B 7/00; H01B 17/34; H01B 17/36; H01B 7/08
USPC ........... 174/117 AS, 113 AS, 117 F; 59/78.1; 29/868
See application file for complete search history.

(56) References Cited

U.S. PATENT DOCUMENTS

| | | | |
|---|---|---|---|
| 4,658,577 A | 4/1987 | Klein | |
| 4,702,281 A | 10/1987 | Moritz | |
| 5,377,892 A | 1/1995 | Kimball | |
| 5,664,957 A | 9/1997 | Starr | |
| 5,759,350 A | 6/1998 | Pyron et al. | |
| 6,546,644 B2 | 4/2003 | Poineau et al. | |
| 7,310,935 B2 | 12/2007 | Worms | |
| 7,388,154 B2 | 6/2008 | Chen et al. | |
| 7,490,500 B2 | 2/2009 | Hernandez, Jr. et al. | |
| 7,520,473 B2 | 4/2009 | Karlinger | |
| 7,784,259 B2 | 8/2010 | O'Rourke et al. | |
| 7,819,034 B2 | 10/2010 | Jasinski | |
| 8,154,859 B2 | 4/2012 | Shahrokhi | |
| 2005/0011665 A1 | 1/2005 | Youngers et al. | |
| 2011/0157663 A1 | 6/2011 | Liu | |
| 2012/0205498 A1 | 8/2012 | Komiya | |
| 2012/0228437 A1 | 9/2012 | Tatsuta et al. | |
| 2013/0075128 A1 | 3/2013 | Kaihotsu et al. | |
| 2014/0042280 A1 | 2/2014 | Takeuchi et al. | |
| 2014/0263866 A1 | 9/2014 | Hemmer | |

OTHER PUBLICATIONS

"Ribbon cable", www.wikipedia.org, Feb. 26, 2013, 4 pages.
(Continued)

*Primary Examiner* — Dion R Ferguson

(57) ABSTRACT

An apparatus includes a cable track configured to be coupled to a moveable object and to be pushed and pulled by the movable object without buckling. The cable track is configured to transport at least one signal or material to or from the moveable object. The cable track has a fluid compartment defined between walls of the cable track. The walls of the cable track are configured to be separated when fluid is inserted into the fluid compartment and to approach one another in a bent portion of the cable track. The cable track may further include a web coupled to the walls, where the web is configured to limit the separation of the walls.

20 Claims, 5 Drawing Sheets

(56) References Cited

OTHER PUBLICATIONS

"High Performance Cable Solutions for the World of Semiconductors", LEONI Elocab Ltd., (No date), 10 pages.

"Flextrack, Self Supporting Flat Cables for the Automation and Robotics Industry", axon cable & interconnect, Nov. 2008, 2 pages.

"CORE High Flex Flat Cable", W.L. Gore & Associates, Inc., Jul. 29, 2010, 2 pages.

"CORE Trackless", W.L. Gore & Associates, Inc., Jul. 30, 2010, 2 pages.

Bradley Humble, "Cable Track for Scanning Head of Paper Machine or Other System", U.S. Appl. No. 13/874,445, filed Apr. 30, 2013.

Notification of Transmittal of the International Search Report and the Written Opinion of the International Searching Authority, or the Declaration dated Jul. 16, 2014 in connection with International Patent Application No. PCT/CA2014/000362.

Notification of Transmittal of the International Search Report and the Written Opinion of the International Searching Authority, or the Declaration dated Jul. 16, 2014 in connection with International Patent Application No. PCT/CA2014/000360.

U.S. Office Action dated Oct. 20, 2014 in connection with U.S. Appl. No. 13/874,445; 12 pages.

U.S. Office Action dated Feb. 27, 2015 in connection with U.S. Appl. No. 13/874,445; 13 pages.

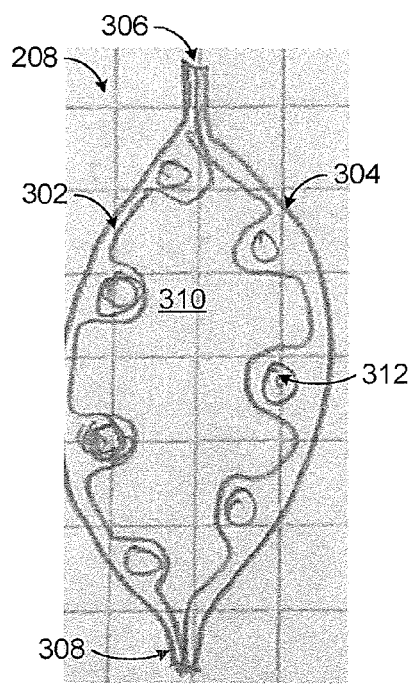
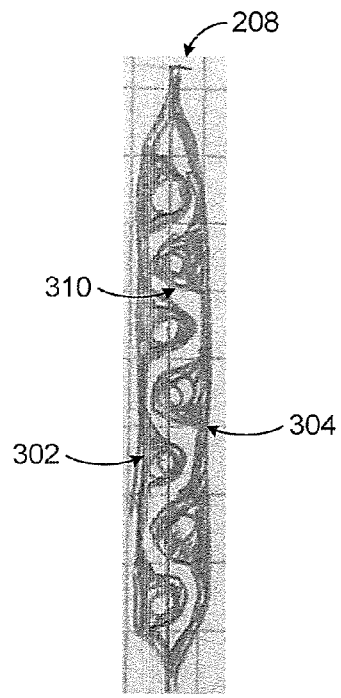
FIGURE 3A          FIGURE 3B
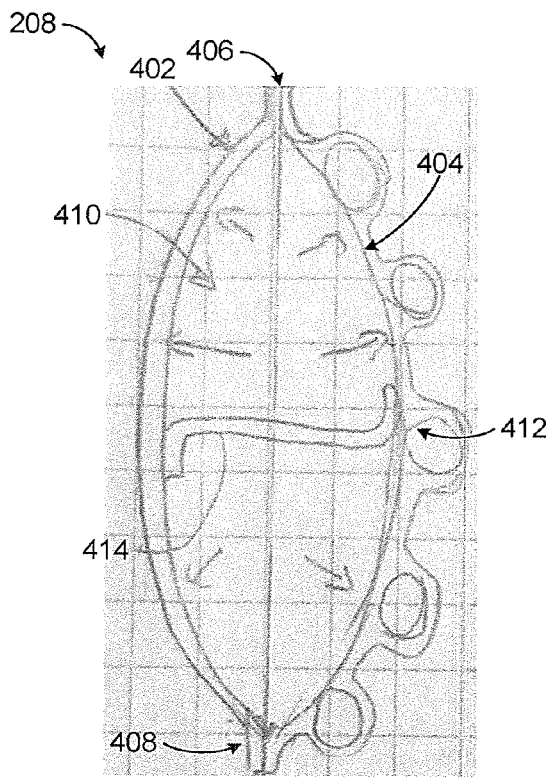
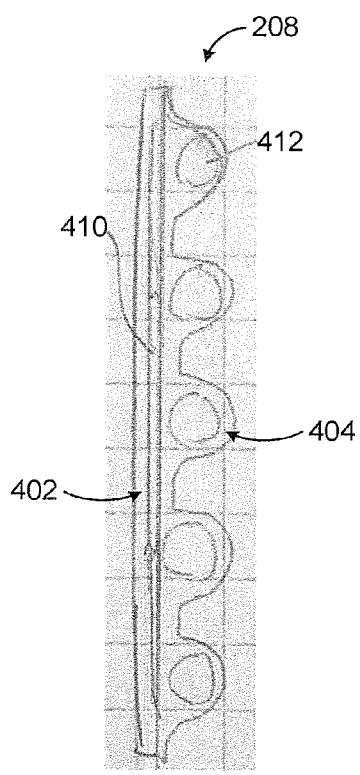
FIGURE 4A          FIGURE 4B

PNEUMATICALLY-EXPANDABLE CABLE TRACK FOR SCANNING HEAD OF PAPER MACHINE OR OTHER SYSTEM

TECHNICAL FIELD

This disclosure relates generally to scanning systems. More specifically, this disclosure relates to a pneumatically-expandable cable track for a scanning head of a paper machine or other system.

BACKGROUND

Webs or other sheets of material are used in a variety of industries and in a variety of ways. These materials can include paper, multi-layer paperboard, and other products manufactured or processed in long sheets. As a particular example, long sheets of paper can be manufactured and collected in reels.

It is often necessary or desirable to measure one or more properties of a sheet of material as the sheet is being manufactured or processed. Adjustments can then be made to the process in order to help ensure that the properties stay within desired ranges. Measurements are often taken using a scanning head that moves back and forth across the width of the sheet. Scanning heads are typically connected to external systems through cable tracks having wires and optionally fluid for the scanning heads. These cable tracks often need to be flexible in at least one direction so that the cable tracks can bend without suffering from fatigue stresses.

When a scanning head moves a relatively short distance, the stiffness of a cable track itself often allows the cable track to be pushed and pulled without the need for a carrier linkage exoskeleton. When a longer cable track is needed, the cable track often cannot be both (i) stiff enough to be pushed without buckling and (ii) flexible enough to allow compact bending. In these situations, a cable track is often placed within a linkage carrier that is designed to resist reverse bending and to provide stiffness so the cable track can be predictably pushed over long distances. However, these linkage carriers add cost, assembly complexity, size, weight, noise, vibration, speed limit, and failure points to the overall system.

SUMMARY

This disclosure provides a pneumatically-expandable cable track for a scanning head of a paper machine or other system.

In a first embodiment, an apparatus includes a cable track configured to be coupled to a moveable object and to be pushed and pulled by the movable object without buckling. The cable track is configured to transport at least one signal or material to or from the moveable object. The cable track has a fluid compartment defined between walls of the cable track. The walls of the cable track are configured to be separated when fluid is inserted into the fluid compartment and to approach one another in a bent portion of the cable track.

In a second embodiment, a system includes a movable object configured to move back and forth and a cable track coupled to the moveable object. The cable track is configured to transport at least one signal or material to or from the moveable object. The cable track has a fluid compartment defined between walls of the cable track. The movable object is configured to push and pull the cable track without buckling the cable track. The walls of the cable track are configured to be separated when fluid is inserted into the fluid compartment and to approach one another in a bent portion of the cable track.

In a third embodiment, a method includes coupling a cable track to a moveable object. The cable track is configured to transport at least one signal or material to or from the moveable object. The method also includes inserting fluid into a fluid compartment defined between walls of the cable track. In addition, the method includes pushing and pulling the cable track with the moveable object without buckling the cable track. The walls of the cable track separate when the fluid is inserted into the fluid compartment and approach one another in a bent portion of the cable track.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which:

FIGS. 2 through 4B illustrate details of example pneumatically-expandable cable tracks used with a scanning head or other movable object according to this disclosure;

DETAILED DESCRIPTION

FIGS. 1 through 8, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
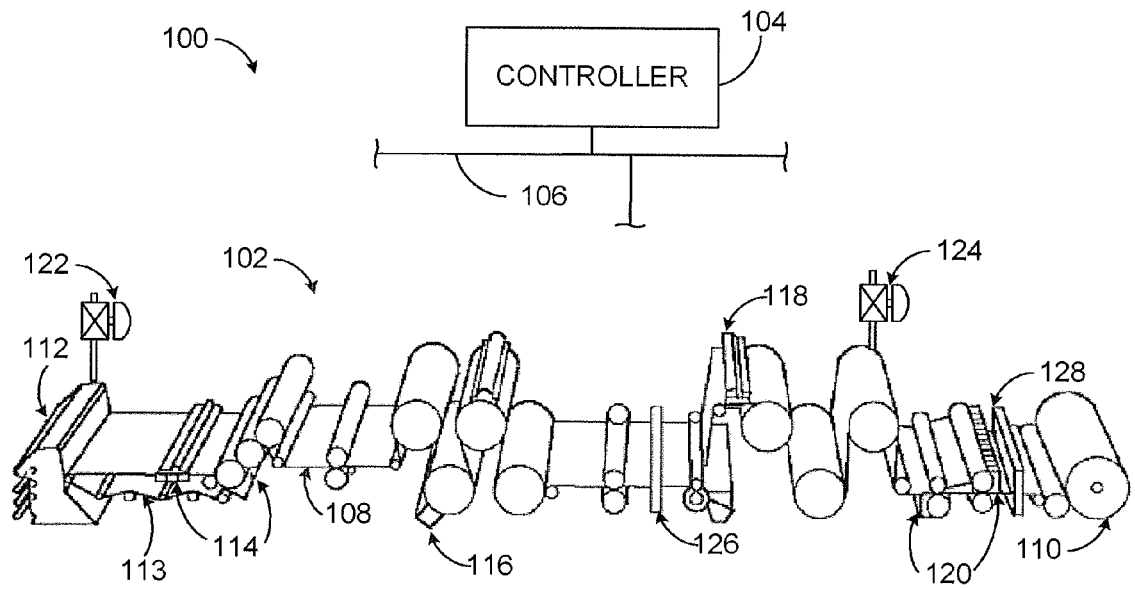
FIG. 1 illustrates an example sheet manufacturing or processing system according to this disclosure.

FIG. 1 illustrates an example sheet manufacturing or processing system 100 according to this disclosure. In this example, the system 100 includes a paper machine 102, a controller 104, and a network 106. The paper machine 102 includes various components used to produce a paper product, namely a paper sheet 108 that is collected at a reel 110. The controller 104 monitors and controls the operation of the paper machine 102, which may help to maintain or increase the quality of the paper sheet 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the sheet. The dilution water may be used to help ensure that the resulting paper sheet 108 has a more uniform basis weight across the sheet 108.

Arrays of drainage elements 114, such as vacuum boxes, remove as much water as possible to initiate the formation of the sheet 108. An array of steam actuators 116 produces hot steam that penetrates the paper sheet 108 and releases the latent heat of the steam into the paper sheet 108, thereby increasing the temperature of the paper sheet 108 in sections across the sheet. The increase in temperature may allow for easier removal of remaining water from the paper sheet 108. An array of rewet shower actuators 118 adds small droplets of water (which may be air atomized) onto the surface of the paper sheet 108. The array of rewet shower actuators 118 may be used to control the moisture profile of the paper sheet 108, reduce or prevent over-drying of the paper sheet 108, or correct any dry streaks in the paper sheet 108.

The paper sheet 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper sheet 108. The arrays of induction heating actuators 120 may therefore be used to control the caliper (thickness) profile of the paper sheet 108. The nips of a calender may also be equipped with other actuator arrays, such as arrays of air showers or steam showers, which may be used to control the gloss profile or smoothness profile of the paper sheet.

Two additional actuators 122-124 are shown in FIG. 1. A thick stock flow actuator 122 controls the consistency of incoming stock received at the headbox 112. A steam flow actuator 124 controls the amount of heat transferred to the paper sheet 108 from drying cylinders. The actuators 122-124 could, for example, represent valves controlling the flow of stock and steam, respectively. These actuators 122-124 may be used for controlling the dry weight and moisture of the paper sheet 108.

Additional components could be used to further process the paper sheet 108, such as a supercalender (for improving the paper sheet's thickness, smoothness, and gloss) or one or more coating stations (each applying a layer of coatant to a surface of the paper to improve the smoothness and printability of the paper sheet). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, the control system described below is not limited to use with systems for producing paper products and could be used with systems that process a paper product or with systems that produce or process other items or materials (such as multi-layer paperboard, cardboard, plastic, textiles, metal webs, or other or additional materials that are manufactured or processed as moving sheets).

In order to control the paper-making process, one or more properties of the paper sheet 108 may be continuously or repeatedly measured. The sheet properties can be measured at one or various stages in the manufacturing process. This information may then be used to adjust the paper machine 102, such as by adjusting various actuators within the paper machine 102. This may help to compensate for any variations of the sheet properties from desired targets, which may help to ensure the quality of the sheet 108.

As shown in FIG. 1, the paper machine 102 includes one or more scanners 126-128, each of which may include one or more sensors. Each scanner 126-128 is capable of measuring one or more characteristics of the paper sheet 108. For example, each scanner 126-128 could include sensors for measuring the caliper, anisotropy, basis weight, color, gloss, sheen, haze, surface features (such as roughness, topography, or orientation distributions of surface features), or any other or additional characteristics of the paper sheet 108.

Each scanner 126-128 includes any suitable structure or structures for measuring or detecting one or more characteristics of the paper sheet 108. For example, each scanner 126-128 could include one or more sets of sensors mounted on a scanning head that moves back and forth across the sheet 108. Note, however, that stationary sensors could also be used at one or more locations of the paper machine 102.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

As described in more detail below, one or more scanners 126-128 could include a cable track connected to a scanning head. The cable track is pneumatically expandable, meaning the cable track can expand in cross-sectional size when a fluid (such as liquid or gas) is placed within the cable track. However, the cable track can return to a flatter shape in the U-shaped portion of the cable track when the cable track is bent. The pneumatic expansion increases the stiffness of the cable track when the cable track is being pushed, and the ability to return to a flatter shape helps to provide compact bending. This allows the cable track to be pulled and pushed repeatedly in a compact space as a scanning head moves back and forth, without requiring the use of carrier linkage exoskeletons or other support structures. This helps to avoid the problems associated with conventional cable track designs.

Although FIG. 1 illustrates one example of a sheet manufacturing or processing system 100, various changes may be made to FIG. 1. For example, other systems could be used to produce other paper or non-paper products. Also, while shown as including a single paper machine 102 with various components and a single controller 104, the system 100 could include any number of paper machines or other machinery having any suitable structure, and the system 100 could include any number of controllers. In addition, FIG. 1 illustrates one operational environment in which a pneumatically-expandable cable track can be used. This functionality could be used in any other type of system, and that system need not manufacture or process moving webs or sheets.

Figure 2:
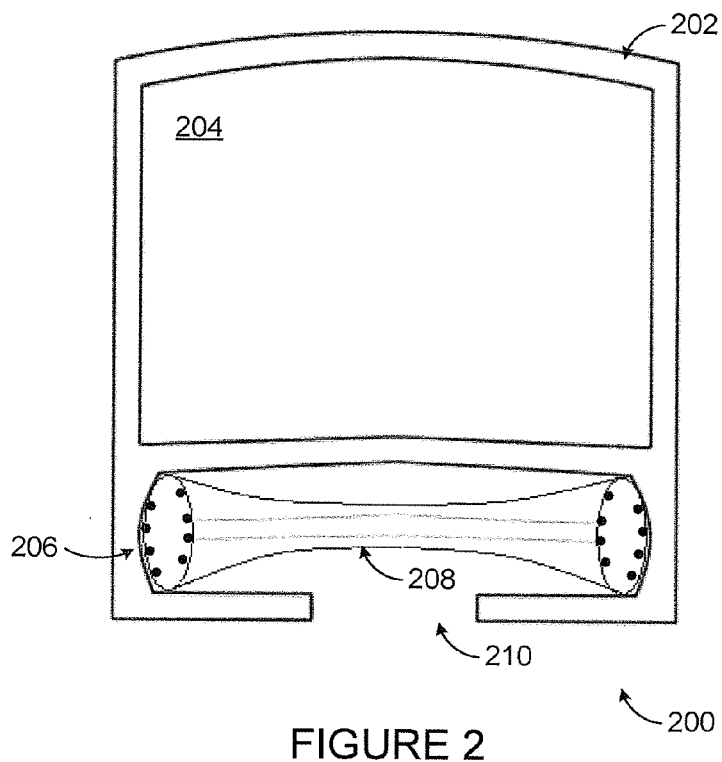

FIGS. 2 through 4B illustrate details of example pneumatically-expandable cable tracks used with a scanning head or other movable object according to this disclosure. FIG. 2 illustrates a cross-section of a structure 200 that supports the use of a cable track. The structure 200 itself could represent an elongated structure that extends any suitable distance, such as the distance across a paper machine 102. In particular embodiments, the structure 200 could form part of one or both scanners 126-128 in the system 100 of FIG. 1.

As shown in FIG. 2, the structure 200 includes a housing 202, which defines an opening 204. The housing 202 is designed to receive a beam or other support through the opening 204. The beam could, for example, represent a beam extending across the upper surface of the sheet 108 in the system 100. By placing the structure 200 onto this beam, the structure 200 is secured in place over the sheet 108.

The structure 200 also defines a second opening 206 below the opening 204. The second opening 206 represents an area where a cable track 208 can be inserted. The cable track 208 represents a structure containing, encasing, or otherwise supporting one or multiple wires, tubes, hoses, or other structures for transporting signals or materials to or from a scanning head or other movable object. The cable track 208 here extends along one side of the opening 206 and then loops back at a "U" bend and extends along another side of the opening 206. The cable track 208 also flattens along the "U" bend.

The housing 202 can be formed from any suitable material(s), such as one or more metals. The housing 202 can also be formed in any suitable manner, such as an extrusion process. In addition, the housing 202 can have any suitable size, shape, and dimensions. The opening 204 can have any suitable size and shape in the housing. The opening 206 can also have any suitable size and shape in the housing.

An opening 210 is provided along the bottom of the housing 202. The opening 210 allows the cable track 208 to exit the opening 206 and couple to a scanning head or other movable object. The movable object could be mounted to or under the housing 202. The opening 210 could have any suitable size and shape. Also, the opening 210 may or may not extend the entire length of the structure 200. In addition, while the opening 210 is shown here as being centered in the cross-section of the structure 200, the opening 210 could be offset to one side or the other in FIG. 2.

As shown in this example, the cable track 208 has an expanded profile or cross-section along the sides of the opening 206 and a flatter profile or cross-section along the "U" bend of the cable track 208. The expanded profile or cross-section can be obtained by placing a fluid (such as liquid or gas) within the cable track 208, possibly under pressure. The flatter profile or cross-section can be obtained when the walls of the cable track 208 push the fluid out of that portion of the cable track 208. Note that the exact forms shown in FIG. 2 are for illustration only. The cable track 208 need not have an elliptical profile or cross-section in its expanded areas, and the profile or cross-section of the cable track 208 in the flattened region could vary.

Example embodiments of the cable track 208 are shown in greater detail in FIGS. 3A through 4B. As shown in FIGS. 3A and 3B, the cable track 208 includes two walls 302-304, which are sealed together along their outer edges 306-308 (although other portions of the walls 302-304 could be sealed together). This creates a fluid compartment 310 between the walls 302-304 as shown in FIG. 3A. The fluid compartment 310 can receive a fluid that pushes the walls 302-304 apart. The cable track 208 can therefore be pneumatically expanded by placing fluid into the compartment 310.

Each wall 302-304 can be formed from any suitable material(s) and in any suitable manner. For example, each wall 302-304 could be formed from a polymer such as polyurethane or polytetrafluoroethylene (PTFE) or from a reinforced fabric. Also, the walls 302-304 can be sealed together in any suitable manner. For instance, if the walls 302-304 are fabricated as separate pieces, the walls 302-304 can be heat-welded together. If the walls 302-304 are formed by folding a single piece of material, the walls 302-304 could be heat-welded along a single edge. The walls 302-304 could also be formed as a single integral unit, such as by an extrusion process that creates the walls 302-304 directly around wires or other components. In this case, a separate operation for sealing the walls 302-304 together may not be needed.

The fluid compartment 310 can have any suitable size and shape, which are defined in part on the relative shapes and sizes of the walls 302-304. For instance, if each wall 302-304 is equal in height, the fluid compartment 310 could assume an elliptical or almost circular shape. If the walls 302-304 are unequal in height, the fluid compartment 310 could assume an irregular shape. In general, the cable track 208 could have any suitable cross-sectional shape that can resist bending when being pushed.

Each wall 302-304 in this example includes one or more pods 312, each of which can be used to transport signals or materials to or from a movable object. For example, wires or wire bundles in the pods 312 can be used to provide signals to and receive signals from a scanning head. As particular examples, wires or wire bundles could be used to supply electrical power and control commands or other data to the scanning head. The wires or wire bundles could also be used to receive measurements and other data from the scanning head. The cable track 208 could include any number of pods 312, and each pod 312 could include any number of wires or wire bundles.

Note that the pods 312 are not limited to simply containing wires. For example, the pods 312 could include one or more hoses, tubes, or other structures configured to transport air, water, or other fluid(s) to or from the scanning head. The pods 312 could also include reinforcing members such as fiberglass, spring metal rods, or other support structures for providing stiffness to the cable track 208. In general, the phrase "cable track" encompasses any suitable track that can transport at least one signal or material to or from a movable object.

Also note that the pods 312 in this example are within both walls 302-304 of the cable track 208. However, pods 312 could be used in only one of the walls 302 or 304. In addition, note that the pods 312 in this example are embedded within the walls 302-304 of the cable track 208. However, other arrangements could also be used. For example, wires, hoses, tubes, or other structures could be secured to the outer and/or inner surface(s) of one or both walls 302-304. A combination of structures fully or partially embedded or contained within one or more walls 302-304 and structures mounted to the surface(s) of one or more walls 302-304 could also be used.

As described above, a portion of the cable track 208 can rotate and flatten when bent, such as in the "U" shaped portion of the cable track 208. This flattening forces fluid out of the compartment 310 and collapses the cable track 208. An example of this is shown in FIG. 3B, where the walls 302-304 have collapsed towards each other and the fluid compartment 310 is much narrower. As can be seen here, the pods 312 in the walls 302-304 are interlaced, and the pods 312 collapse along a neutral axis of the cable track 208. This helps to provide more even bend stresses on the pods 312 by reducing the difference between the inside and outside bend radii of the cable track 208.

As shown in FIGS. 4A and 4B, the cable track 208 includes two walls 402-404 sealed together along their edges 406-408 to create a fluid compartment 410. As shown in FIG. 4A, the fluid compartment 410 can receive a fluid that pushes the walls 402-404 apart. The cable track 208 can therefore be pneumatically expanded by placing fluid into the compartment 410.

Each wall 402-404 can be formed from any suitable material(s) and in any suitable manner. Example materials and techniques are described above with respect to the walls 302-304. Also, the fluid compartment 410 can have any suitable size and shape, which are defined in part on the relative shapes and sizes of the walls 402-404. In general, the cable track 208 could have any suitable cross-sectional shape that can resist bending when being pushed. A single wall 404 in this example includes one or more pods 412, each of which can include one or more wires, hoses, tubes, reinforcing members, or other structures. The other wall 402 here does not contain any pods.

Once again, note that the pods 412 in this example are embedded within the wall 404 of the cable track 208. However, other arrangements could also be used. For example, wires, hoses, tubes, or other structures could be secured to the outer and/or inner surface(s) of the wall 404. A combination of structures fully or partially embedded or contained within the wall 404 and structures mounted to the surface(s) of the wall 404 could also be used.

As described above, the cable track 208 can rotate and flatten when bent, such as in the "U" shaped portion of the cable track 208. This flattening forces fluid out of the compartment 410 and collapses the cable track 208. An example of this is shown in FIG. 4B, where the walls 402-404 have collapsed towards each other and the fluid compartment 410 is much smaller. As can be seen here, the pods 412 in the wall 404 collapse along a neutral axis of the cable track 208. This helps to provide more even bend stresses on the pods 412.

In this example, one or more webs 414 can be used to limit the expansion of the cable track 208. For example, each web 414 can be coupled to both walls 402-404 of the cable track 208. When the walls 402-404 are close to each other, the web 414 can hang loosely from the walls. When the walls 402-404 move away from each other, the web 414 can be pulled tight and prevent further movement of the walls 402-404 away from each other. This can help to maintain a desired shape of the cable track 208. Each web 414 includes any suitable structure for limiting movement in a cable track. Although not shown, one or more webs 414 can also be used in the cable track 208 of FIGS. 3A and 3B. Each web 414 can be formed from any suitable material(s) and in any suitable manner. Each web 414 can also be secured to the walls of a cable track in any suitable manner.

The height, width, and curvature(s) of each cable track 208 and the pressure of the fluid within each cable track 208 could be varied to obtain the desired flexibility and stiffness of the cable track for a given application. Surface and wear features can also be added to each cable track 208. A wear surface could be placed along any portion of the cable track that could wear against another structure.

Although FIGS. 2 through 4D illustrate details of example pneumatically-expandable cable tracks 208 used with a scanning head or other movable object, various changes may be made to FIGS. 2 through 4D. For example, while shown as being used within the structure 200, the cable tracks 208 could be used with any other suitable device.

Figure 5:
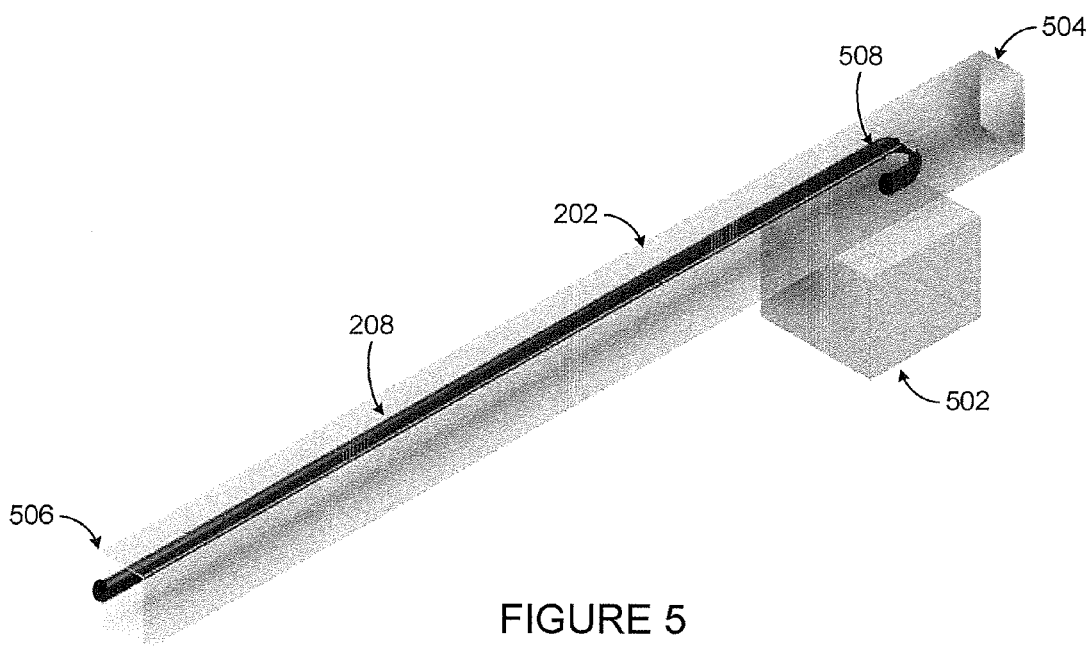
FIGS. 5 through 7 illustrate example operations of a pneumatically-expandable cable track used with a scanning head or other movable object according to this disclosure.
Figure 6:
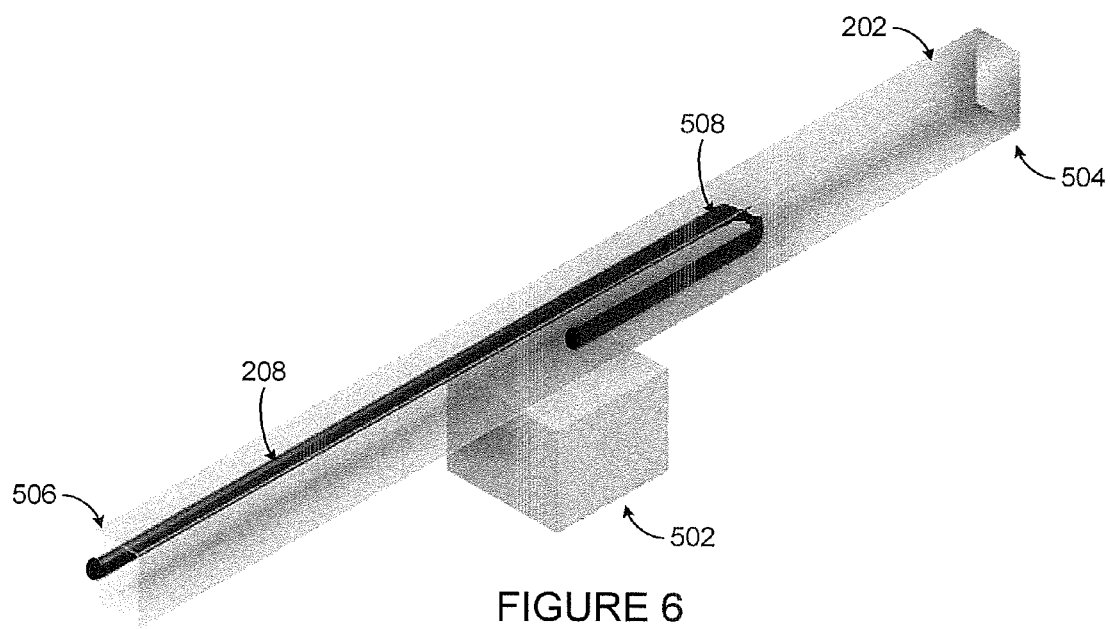
Figure 7:
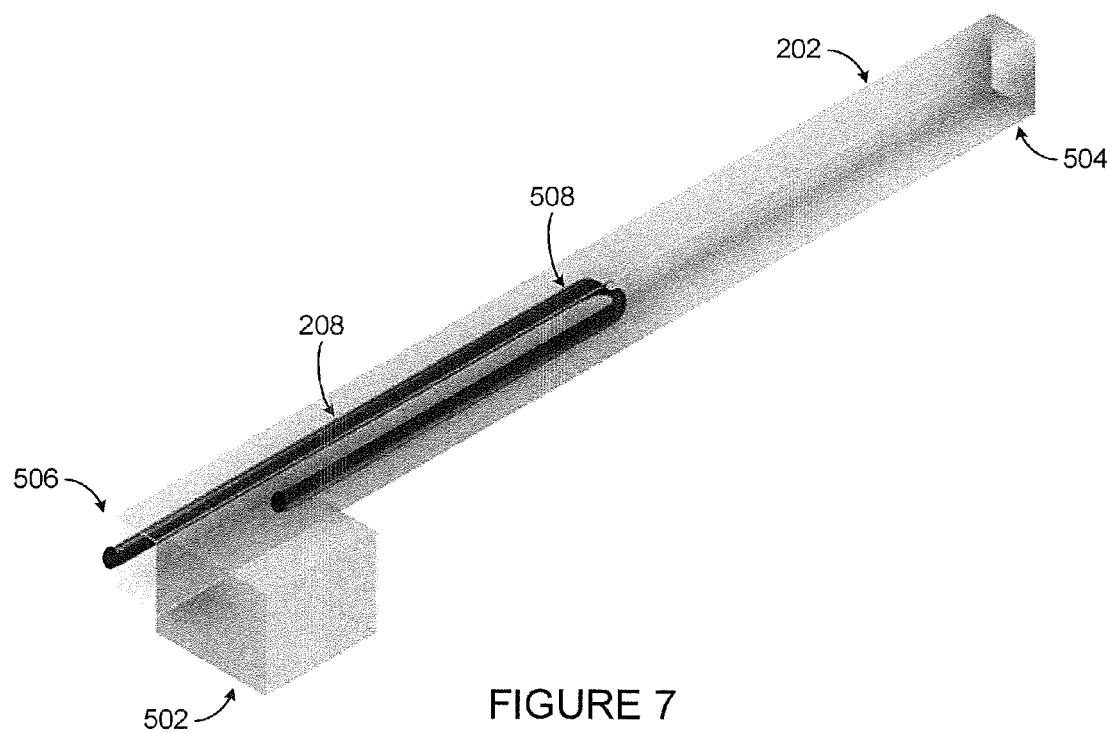

FIGS. 5 through 7 illustrate example operations of a cable track 208 used with a scanning head or other movable object according to this disclosure. In particular, FIGS. 5 through 7 illustrate a scanning head 502 moving along under the housing 202. Note that the scanning head 502 could be mounted on the housing 202 itself or under the housing 202.

In FIG. 5, the scanning head 502 is positioned near a first end 504 of the housing 202. One end of the cable track 208 can be secured to an object at or near a second end 506 of the housing 202. The other end of the cable track 208 can be secured to the scanning head 502. Fittings or other structures can be used to help prevent fluid leakage from the cable track 208 and to maintain fluid pressure within the cable track 208. In this position, the cable track 208 has a "J" shape, meaning the cable track 208 extends along one side of the housing 202, makes a "U" bend 508, and extends a short way along the other side of the housing 202.

In FIG. 6, the scanning head 502 has moved approximately halfway along the housing 202. During this movement, the scanning head 502 pulls on the cable track 208. At this point, the cable track 208 has a shape somewhat between a "J" shape and a "U" shape. The cable track 208 still makes the "U" bend 508, but the "U" bend 508 is now in a different location of the cable track 208.

In FIG. 7, the scanning head 502 has moved near the second end 506 of the housing 202. Again, during this movement, the scanning head 502 pulls on the cable track 208. The cable track 208 is now substantially "U" shaped. Again, the cable track 208 still makes the "U" bend 508, but the "U" bend 508 is in a different location of the cable track 208.

The scanning head 502 then traverses back across the housing 202 towards the first end 504 of the housing 202. During this movement, the scanning head 502 pushes on the cable track 208. As a result, the cable track 208 can assume the configuration shown in FIG. 6 since the scanning head 502 is pushing the cable track 208. Eventually, the cable track 208 can assume the configuration shown in FIG. 5 when the scanning head 502 reaches the first end 504 of the housing 202. This process can repeat any number of times as the scanning head 502 moves back and forth.

As can be seen in FIGS. 5 through 7, the cable track 208 is able to be coupled to an object moving back and forth without requiring the use of carrier linkages or other support structures. This helps to eliminate the costs, delays, and undesirable effects associated with the use of carrier linkages. Ordinarily, the lack of carrier linkages would cause a conventional cable track to buckle when it is being pushed. The force required to buckle a column is proportional to the column's modulus of elasticity and moment of inertia and is inversely proportional to the square of the column's length. When used with respect to a cable track, this can be expressed as $F \propto EI/L^2$, where E represents the modulus of elasticity of the cable track, I represents the smaller of the two area moments of inertia of the cross section of the cable track, and L represents the length of the cable track. Stiffness is defined as the product of "E" and "I".

Increasing the "I" value can be achieved in a number of ways, such as by altering the size and shape of the cross section of the cable track. However, increasing the stiffness of the cable track, particularly in the direction of the "U" bend, increases the natural bend radius of the cable track, thus requiring a larger area for the cable track. It could also cause excessive stresses within the cable track and ultimately lead to failure.

Using a pneumatically-expandable cable track 208 provides suitable stiffness to resist buckling while allowing the cable track 208 to flatten out around the "U" bend 508, reducing the bend radius and temporarily reducing the "I" value and the associated stresses within the cable track. The cable track 208 can return to its original shape on either side of the "U" bend 508. Moreover, separating the walls of the cable track 208 via injection of fluid into the cable track's fluid compartment 310, 410 separates wires and other structures from a centerline of the cable track 208, increasing the "I" value in the expanded portions of the cable track and allowing longer cable lengths to be pushed before buckling occurs.

Although FIGS. 5 through 7 illustrate example operations of a pneumatically-expandable cable track 208 used with a scanning head or other movable object, various changes may be made to FIGS. 5 through 7. For example, the cable track 208 here is used in an orientation where the "U" and "J" shapes are generally horizontal within the housing 202. However, the cable track 208 is not limited to this particular orientation. The cable track 208 could be used in an orientation where the "U" and "J" shapes are generally vertical or in any other suitable orientation.

Figure 8:
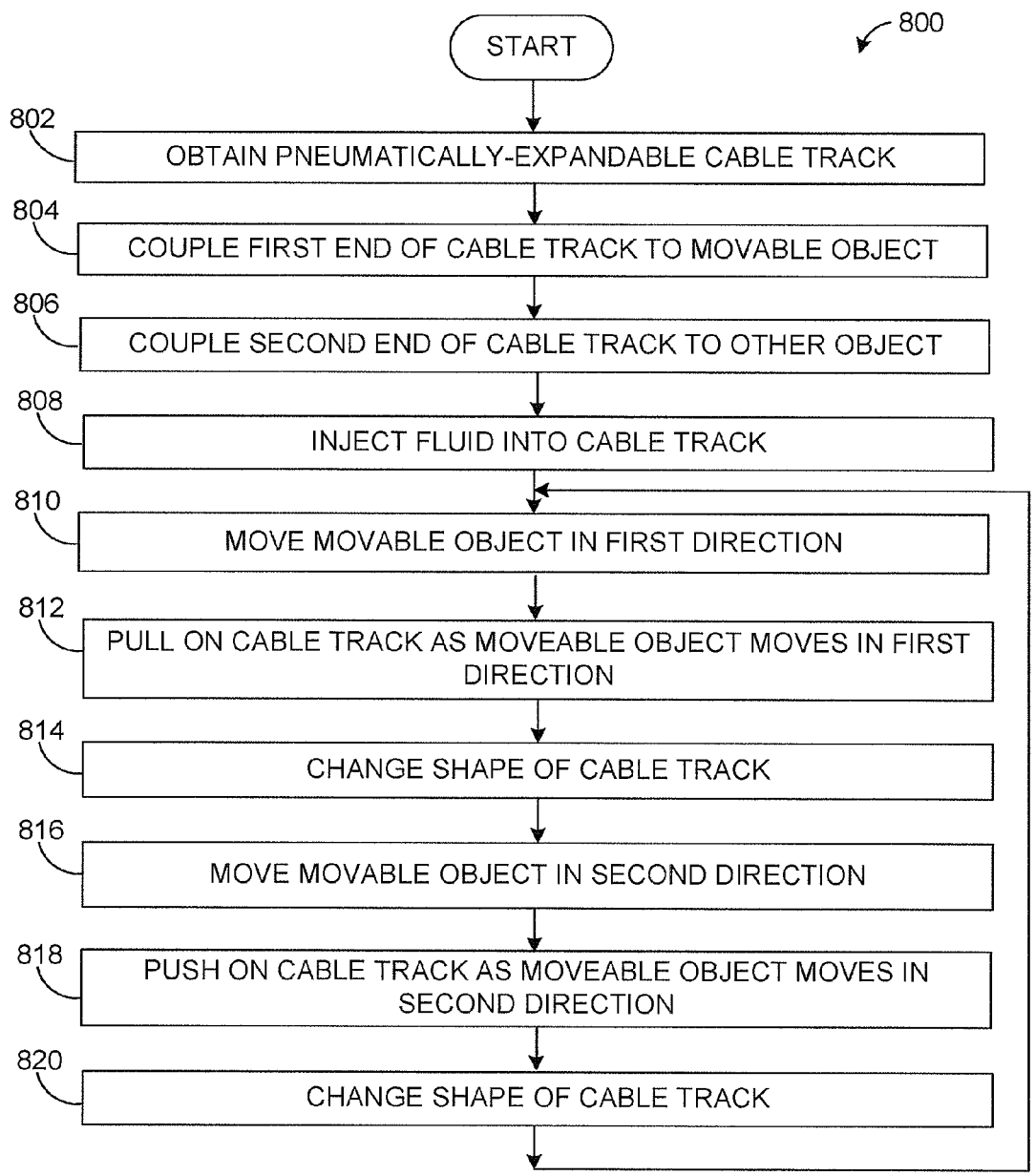
FIG. 8 illustrates an example method for using a pneumatically-expandable cable track with a scanning head or other movable object according to this disclosure.

FIG. 8 illustrates an example method 800 for using a pneumatically-expandable cable track with a scanning head or other movable object according to this disclosure. As shown in FIG. 8, a pneumatically-expandable cable track is obtained at step 802. This could include, for example, obtaining a cable track 208 with the appropriate number(s) and type(s) of wires or other pod contents for a desired application.

A first end of the cable track is coupled to a movable object at step 804, a second end of the cable track is coupled to another object at step 806, and fluid is injected into the cable track at step 808. This could include, for example, coupling wires in the cable track 208 to a scanning head 402 or other movable object. This could also include coupling the wires in the cable track 208 to another portion of a sheet-making or sheet-processing system. This could further include injecting water, air, or other liquid or gas into the cable track 208. The liquid or gas may or may not be injected or maintained at elevated pressure during use of the cable track 208. Suitable fittings can be used on either end of the cable track 208 to prevent leakage of the fluid and to maintain fluid pressure within the cable track 208.

The movable object is moved in a first direction at step 810. This could include, for example, moving the scanning head 502 in a first direction over a sheet 108. During this time, the movable object pulls on the cable track as the movable object moves in the first direction at step 812, which changes the shape of the cable track at step 814. This could include, for example, the scanning head 502 pulling on the cable track 208 to change the shape of the cable track 208 from a "J" shape to a "U" shape. This could also include the "U" bend 508 of the cable track 208 changing locations along the cable track 208.

The movable object is moved in a second direction at step 816. This could include, for example, moving the scanning head 502 in a second direction over the sheet 108. During this time, the movable object pushes on the cable track as the movable object moves in the second direction at step 818, which changes the shape of the cable track at step 820. This could include, for example, the scanning head 502 pushing on the cable track 208 to change the shape of the cable track 208 from a "U" shape to a "J" shape. This could also include the "U" bend 508 of the cable track 208 changing locations along the cable track 208.

Steps 810-820 can be repeated any number of times as the movable object moves back and forth repeatedly. In a paper machine 102 or other sheet-making or sheet-processing system, the scanning head 502 could move back and forth many thousands of times, possibly even hundreds of thousands or millions of times during its operational lifetime.

Although FIG. 8 illustrates one example of a method 800 for using a cable track with a scanning head or other movable object, various changes may be made to FIG. 8. For example, while shown as a series of steps, various steps in FIG. 8 could overlap, occur in parallel, occur in a different order, or occur any number of times. As a particular example, steps 810-814 could all occur generally at the same time, and steps 816-820 could all occur generally at the same time.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
    a cable track configured to be coupled to a moveable object and to be pushed and pulled by the movable object without buckling, the cable track configured to transport at least one signal or material to or from the moveable object;
    the cable track having a fluid compartment defined between walls of the cable track;
    wherein the walls of the cable track are configured to be separated when fluid is inserted into the fluid compartment and to approach one another in a bent portion of the cable track.

2. The apparatus of claim 1, wherein at least one of the walls of the cable track includes or is coupled to multiple pods, the pods configured to transport the at least one signal or material to or from the moveable object.

3. The apparatus of claim 2, wherein the walls are configured such that the pods are substantially aligned along a neutral axis when the cable track is flattened in the bent portion of the cable track.

4. The apparatus of claim 2, wherein multiple pods are embedded within one or more walls of the cable track.

5. The apparatus of claim 1, wherein the cable track further comprises a web coupled to the walls, the web configured to limit the separation of the walls.

6. The apparatus of claim 1, wherein:
    the bent portion of the cable track comprises a "U" bend in the cable track; and
    the cable track is configured to be pushed and pulled without buckling to change a location of the "U" bend along the cable track.

7. The apparatus of claim 1, wherein the cable track is configured to change shape repeatedly between a "J" shape and a "U" shape.

8. The apparatus of claim 1, further comprising:
    a housing comprising first and second openings, the first opening configured to be secured to a support structure, the second opening configured to receive the cable track.

9. A system comprising:

a movable object configured to move back and forth; and a cable track coupled to the moveable object, the cable track configured to transport at least one signal or material to or from the moveable object, the cable track having a fluid compartment defined between walls of the cable track;

wherein the movable object is configured to push and pull the cable track without buckling the cable track; and wherein the walls of the cable track are configured to be separated when fluid is inserted into the fluid compartment and to approach one another in a bent portion of the cable track.

10. The system of claim 9, wherein at least one of the walls of the cable track includes or is coupled to multiple pods, the pods configured to transport the at least one signal or material to or from the moveable object.

11. The system of claim 10, wherein the walls are configured such that the pods are substantially aligned along a neutral axis when the cable track is flattened in the bent portion of the cable track.

12. The system of claim 9, wherein:

the bent portion of the cable track comprises a "U" bend in the cable track; and the cable track is configured to be pushed and pulled without buckling to change a location of the "U" bend along the cable track.

13. The system of claim 9, wherein the cable track further comprises a web coupled to the walls, the web configured to limit the separation of the walls.

14. The system of claim 9, further comprising:

a housing comprising first and second openings, the first opening configured to be secured to a support structure, the second opening configured to receive the cable track.

15. The system of claim 9, wherein the movable object comprises a scanning head configured to measure one or more characteristics of a sheet of material.

16. A method comprising:

coupling a cable track to a moveable object, the cable track configured to transport at least one signal or material to or from the moveable object;

inserting fluid into a fluid compartment defined between walls of the cable track; and pushing and pulling the cable track with the moveable object without buckling the cable track;

wherein the walls of the cable track separate when the fluid is inserted into the fluid compartment and approach one another in a bent portion of the cable track.

17. The method of claim 16, wherein at least one of the walls of the cable track includes or is coupled to multiple pods, the pods configured to transport the at least one signal or material to or from the moveable object.

18. The method of claim 17, wherein the walls are configured such that the pods are substantially aligned along a neutral axis when the cable track is flattened in the bent portion of the cable track.

19. The method of claim 16, wherein the cable track further comprises a web coupled to the walls, the web limiting the separation of the walls.

20. The method of claim 16, wherein:

the movable object comprises a scanning head; and the method further comprises measuring one or more characteristics of a sheet of material using the scanning head.

* * * * *